United States Patent [19]

Hofstadt et al.

[11] 4,398,050

[45] Aug. 9, 1983

[54] PROCESS FOR THE PRODUCTION OF OLEFINS FROM SYNTHESIS GAS

[75] Inventors: Carl-Ernst Hofstadt, Munich; Michael Schneider, Ottobrunn-Riemerling; Karel Kochloefl, Moosburg, all of Fed. Rep. of Germany

[73]* Assignee: Süd Chemie, A.G., Munich, Fed. Rep. of Germany

[21] Appl. No.: 234,477

[22] Filed: Feb. 17, 1981

[30] Foreign Application Priority Data

Feb. 14, 1980 [DE] Fed. Rep. of Germany ....... 3005550

[51] Int. Cl.$^3$ .............................................. C07C 1/04
[52] U.S. Cl. .................................. 585/640; 568/909; 585/639
[58] Field of Search ................. 585/639, 640; 568/909

[56] References Cited

U.S. PATENT DOCUMENTS

| 2,636,057 | 4/1953 | Cutcher et al. | 585/640 |
|---|---|---|---|
| 4,049,741 | 9/1977 | Kuo et al. | 585/640 X |
| 4,076,761 | 2/1978 | Chang et al. | 585/640 X |
| 4,260,841 | 4/1981 | Holland et al. | 585/640 X |

FOREIGN PATENT DOCUMENTS

| 43-481 | 1/1968 | Japan | 585/640 |
|---|---|---|---|
| 917047 | 1/1963 | United Kingdom | 585/640 |

OTHER PUBLICATIONS

Natarajan et al., "Alumina Catalyst for Alcohol Dehydration," Indian J. Tech., vol. 10, Dec., 1972, pp. 463-464.

*Primary Examiner*—Thomas A. Waltz
*Attorney, Agent, or Firm*—William R. Price

[57] ABSTRACT

A process for the production of olefins from synthesis gas comprises a first synthesis stage in which a mixture of methanol and higher alcohols are formed from a synthesis gas comprising hydrogen and carbon monoxide. The catalyst for the first synthesis stage comprises the oxides of copper and zinc in intimate association with each other and a promoting compound selected from the group consisting of chromium, cerium, lanthanum, manganese, thorium, and an alkali metal. The materials from the first synthesis stage are separated into a gas phase and a liquid phase. Thereafter the methanol is separated from the higher alcohol fractions. The higher alcohols are then subjected to dehydration in a dehydration stage which comprises passing the higher alcohol fraction over an alkalized dehydration catalyst at a pressure in the range of 0.5–1 bar and a temperature in the range of 350°–500° C. Thereafter the olefins produced by the dehydration of the higher alcohols are separated into the olefinic and non-olefinic materials. Preferred dehydration catalysts include alkalized aluminum oxide and alkalized calcium phosphate.

21 Claims, No Drawings

PROCESS FOR THE PRODUCTION OF OLEFINS FROM SYNTHESIS GAS

FIELD OF THE INVENTION

This invention relates to a process for the production of olefins. More particularly, this invention relates to a two stage process wherein olefins are produced from synthesis gas. Still more particularly, this invention relates to the production of alcohols from synthesis gas containing hydrogen and carbon monoxide in a first stage followed by conversion of the alcohols to olefins in a second dehydration stage.

BACKGROUND OF THE INVENTION

Low aliphatic olefins, in particular ethylene and propene, are today among the most important basic materials of organic chemistry. Both olefins are produced on an industrial scale today exclusively by thermal splitting of saturated hydrocarbons, different raw materials being available in various countries. Thus for example in Western Europe more than 80% of the ethylene is obtained from naphtha, about 10 to 15% by gas oil splitting, and the balance from high-ethane petroleum. The olefin production is entirely dependent on imported petroleum. To alleviate the dependence of the petrochemical industry on petroleum import, new methods are being adapted for the production of olefins from synthesis gas and hydrogen.

DESCRIPTION OF THE PRIOR ART

As is known, ethylene can be produced by hydrogenation of carbon monoxide by means of cobalt, nickel, or platinum catalysts according to German Pat. No. 1,271,098. However, the profitability of the method is limited by too low a yield of ethylene.

Another method of synthesizing olefins is the well-known Fischer-Tropsch synthesis. Because with the use of the usual iron catalysts the olefins formed only a small portion of the product spectrum, iron catalysts have been promoted with $V_2O_5$ and ZnO or MnO and ZnO (DE-OS No. 25 18 964) or only with MnO (DE-OS No. 25 07 647), to increase the olefin formation. Thus e.g. a manganese-containing iron-catalyst produces at 265° C. and a pressure of 10.6 bar from a synthesis gas of 54.4 vol.% CO and at a space velocity of 310 liters of synthesis gas per hour and liter of catalyst 8 g ethylene and 28.2 g propene per $Nm^3$. In addition there are formed 18.8 g butenes, 26.5 g paraffins, 59.8 g liquid products and 198.3 g $CO_2$ per $Nm^3$ synthesis gas, with a total CO conversion of 81%. The selectivity of ethylene and propene formation is only about 11%. Due to the rather low selectivity, this process would be profitable only if the other products could be utilized.

SUMMARY OF THE INVENTION

It is the object of the invention to make available a process for the production of olefins, in particular ethylene and propene, by dehydration of aliphatic alcohols, wherein one can start with coal-based primary materials.

The process according to the invention is characterized in that (a) from gases containing carbon monoxide and hydrogen, such as synthesis gas, using a catalyst on the basis of a starting catalyst which contains copper oxide, zinc oxide and possibly aluminum oxide and/or potassium oxide and which is promoted with chromium, cerium, lanthanum, manganese, thorium or a combination of these elements, an alcohol mixture containing methanol and higher aliphatic alcohols is produced; (b) from this alcohol mixture the methanol is separated; (c) the higher aliphatic alcohols, in particular ethanol and the propanols, are dehydrated with a dehydration catalyst to the respective olefins; and (d) the obtained olefin mixture is fractionated if desired.

DETAILED DESCRIPTION OF THE INVENTION

The promoted catalyst used according to the invention in step (a) is the subject of our German co-pending application P No. 30-05-551.7 (filed Feb. 14, 1980, and U.S. patent application filed concurrently herewith). This catalyst is obtainable by either coprecipitating from a solution comprising soluble salts of copper, zinc and possibly aluminum to which soluble salts of promotor compounds could be added an insoluble precipitate which is calcined after removal of the extraneous ions; or (b) impregnating a mixture of the oxides of copper, zinc and possibly aluminum with solutions of the promotor compounds and calcining the product obtained. The promotor compounds comprise compounds of chromium, cerium, lanthanum, manganese, or of combinations of these elements. The compound of potassium may be added in any desired production step.

The starting catalysts used for the production of this promoted catalyst contain about 18–45 wt.%, preferably about 25–40 wt.% copper oxide; about 24–50 wt.%, preferably about 30–45 wt.% zinc oxide; about 5–25 wt.%, preferably about 1.7–2.5 wt.% potassium (calculated as $K_2O$), promotor compounds being present in this catalyst in quantities of about 1–25 wt.%, preferably about 3–18 wt.% (calculated as oxides).

Preferably these promoted catalysts are produced (a) by precipitation from a solution of the water-soluble salts, of copper and zinc and the promotor elements, (preferably nitrates) through the addition of alkali carbonate, at a temperature of about 60° to 70° C. The precipitate produced is separated, washed and dried; or (b) an oxide mixture obtained by thermal decomposition of a copper-zinc-amminocarbonate solution in the presence of suspended aluminum oxide may be impregnated with salts, preferably nitrates, of the promotor elements. The products obtained according to (a) or (b) are calcined at about 350° to 450° C., preferably at about 380° to 400° C.

Further, the starting catalysts containing the promoter compounds may be subjected to a re-impregnation with a potassium compound and to a recalcination, the potassium content (calculated as $K_2O$) being about 0.03 to 3.4 wt.%, preferably about 1.7 to 2.5 wt.%.

Potassium hydroxide, potassium carbonate, potassium hydrogen carbonate, potassium acetate, potassium chromate or dichromate, or their mixtures may be used. The recalcination can be carried out at about 350° to 450°, preferably at about 380° to 400° C.

For activation these promoted catalysts are then subjected to a reducing after-treatment, which is carried out first with the aid of an inert gas, such as nitrogen, containing a small amount of hydrogen. Then the hydrogen component is gradually increased, the temperature being simultaneously increased gradually from about 170° to about 350° C., until in the end pure hydrogen is used for the reduction.

The promoted catalysts of our German patent application No. P 30 05 551.7 are used for the synthesis of alcohol mixtures containing methanol and higher alcohols, which can be used as fuel or fuel additive for Otto engines.

According to the present invention, such alcohol mixtures serve as raw materials for the production of olefins. By selective promotion with chromium, and manganese, and by the selection of suitable reaction conditions, the formation of the $C_2$ and $C_3$ alcohols can be controlled.

In step (a) of the process of the invention, a synthesis gas containing about 25 to 30 vol.%, preferably about 27 vol.% CO, 0 to 15 vol.% $N_2$, 0 to 4 vol.% $CO_2$, 0 to 7 vol.% $CH_4$, balance $H_2$, may be reacted at about 250° to 400° C., preferably 350° C., at a pressure of about 80 to 150 bar, preferably about 100 bar, and at a space velocity of about 500 to 5000, preferably about 1500 liters of gas per hour and liter of catalyst, over the promoted catalyst to produce the alcohol mixture.

Preferably the reaction of the synthesis gas in step (a) is carried out in tube reactors swept by cooling medium or in full-space reactors with cold gas cooling, both reactor systems being operated with recycling if desired.

The alcohol mixture obtained in step (a) is fractionated in step (b) using one or more distillation columns into low-boiling by-products and methanol, on the one hand, and higher alcohols and water, on the other. Hence one obtains besides the desired $C_2$ and $C_3$ alcohol fraction also pure methanol as well as a mixture of aliphatic $C_4$ to $C_6$ alcohols with only small proportions of by-products.

According to the invention, the dehydration of the higher aliphatic alcohols in step (c) is carried out with the usual dehydration catalysts, for example $Al_2O_3$, $SiO_2$, $TiO_2$, $AlPO_4$ or $Ca_3(PO_4)_2$. Preferably one carries out the dehydration with alkalized aluminum oxide or calcium phosphate, in order to suppress secondary reactions, e.g. condensations and polymerizations of the olefins. The dehydration is carried out preferably at atmospheric or reduced pressure of about 0.5 to 1 bar, preferably about 0.75 bar, at a temperature of about 350° to 500° C., preferably about 400° to 450° C., and at a space velocity of about 1 to 7, preferably about 2-4 liters of alcohol mixture per hour and liter of catalyst.

Aluminum oxide or calcium phosphate may be alkalized by impregnation with aqueous solutions of the alkali hydroxides or alkali carbonates, preferably of the hydroxides, such as LiOH, KOH, NaOH, preferably LiOH. The alkali metal concentration of said solutions should be in the range of about 0.1 to 1.5 wt.%, preferably about 0.3 to 0.8 wt.%.

The selection of suitable reaction conditions (temperature about 400° to 450° C. and space velocities of about 2.0 to 2.5 kg alcohol mixture per hour and liter of catalyst) permits reactions up to 91 mol.% and a selectivity of about 98%.

The reaction mixture obtained from step (c) is first cooled in step (d), preferably to a temperature of about 10° C.; then it is prefractionated into liquid and gaseous products, whereupon the gaseous components freed from water are further fractionated by low-temperature distillation and the liquid components by distillation or extractive distillation. By low-temperature distillation ethylene and propene can be obtained in pure form.

Since the pure methanol and the aliphatic $C_4$ to $C_6$ alcohols are usable (for example as solvents or plasticizers), the profitability of the entire process is thus increased.

Two examples of the preparation of dehydration catalysts suitable for use in step (c) of the present process are presented hereafter.

PREPARATION OF DEHYDRATION CATALYST I

Aluminum oxide hydrate powder was mixed with 3.6% of its weight in aluminum stearate and compacted to cylindrical pellets of a height of 4.5 mm and a diameter of 4.5 mm by means of a pelletizing machine. The tablets were calcined in air for 4 hours at 510° C.

100 g of the calcined pellets were immersed at room temperature in an aqueous solution of 10 g LiOH in 435 ml water for 20 minutes and then dried at 120° C. for 2 hours and calcined at 400° C. for 2 hours. The product contained 0.29% Li and had a BET surface of 210 $m^2/g$.

PREPARATION OF DEHYDRATION CATALYST II

Tricalcium phosphate was mixed with 3.6% of its weight in aluminum stearate and compacted to cylindrical pellets of a height of 4.5 mm and a diameter of 4.5 mm by means of a pelletizing machine. The pellets were calcined in air for 4 hours at 510° C. 100 g of the calcined pellets were immersed at room temperature in an aqueous solution of 10 g LiOH in 166 ml water for 20 minutes and then dried at 120° C. for 2 hours and calcined at 400° C. for 2 hours. The product contained 0.28% Li and had a BET surface of 38.7 $m^2/g$.

The process according to the invention is explained in a non-limiting manner with reference to the following examples.

EXAMPLE 1

In a tube reactor (tube diameter 18 mm, tube length 1000 mm) heated with a liquid medium were charged 30 ml of a promoted catalyst A compacted to pellets of the dimensions 3×3 mm, which catalyst had been obtained according to the procedure of Example 7 of our German Patent Application No. P 30 05 551.7 and whose composition is given in Table I. Catalyst A was activated with a gas consisting of 1.2 vol.% $H_2$, balance $N_2$, for 40 hours at 145° to 350° C. The temperature rise was about 5° C. per hour. After reaching 350° C., the catalyst to be tested was treated with pure hydrogen for another 5 hours. Then synthesis gas having a composition of CO 29.0 vol.%
$CO_2$ 1.5 vol.%
$CH_4$ 1.4 vol.%
$N_2$ 5.0 vol.%
$H_2$ balance was supplied to the reactor and a pressure of 100 bar and a space velocity of 2000 liters synthesis gas per hour and liter of catalyst were adjusted. The results and the composition of the reaction products are summarized in Tables II and III.

The liquid products obtained by condensation at 10° C. were processed by distillation so that a fraction consisting of ethanol and propanols was obtained and subsequently subjected to dehydration. The composition of this fraction is given in Table IV.

The dehydration of the alcohol mixture was carried out at 400° C., a pressure of 1 bar and a space velocity of 2.5 kg alcohol mixture per hour and liter of catalyst in an electrically heated tube reactor of a tube diameter of 25 mm and a tube length of 500 ml (sic), charged with 50 ml dehydration catalyst I.

After condensation at 10° C., the gaseous products were dried and subjected to a low-temperature distillation, while the liquid products were subjected to extractive distillation. The results of the dehydration and the composition of the individual fractions are given in Table V.

EXAMPLE 2

The procedure of Example 1 was repeated with the difference that for the production of a mixture of methanol and higher aliphatic alcohols catalyst C was used, the preparation of which is described in Example 5 of patent application No. P 30 05 551 and its composition given in Table I. The results and the composition of the reaction products are given in Tables II and III. The composition of the ethanol-propanol fraction obtained by distillation (step (b)) is given in Table IV. This fraction was dehydrated according to the procedure of Example 1, and the olefin mixture obtained was fractionated.

EXAMPLE 3

The procedure of Example 1 was repeated with the difference that for the preparation of a mixture of methanol and higher aliphatic alcohols catalyst D was used, the preparation of which is described in Example 2 of our German patent application No. P 30 05 551 and its composition is shown in Table I. The results and the composition of the reaction products are provided in Tables II and III. The composition of the ethanol-propanol fraction obtained by distillation is given in Table IV. The dehydration and fractionation were carried out as in Example 1. The results of the dehydration and the composition of the individual fractions are all shown in Table V.

EXAMPLE 4

The dehydration of an ethanol-propanol fraction obtained according to the procedure of Example 1 was carried out at 450° C., at a pressure of 1 bar and a space velocity of 2.0 kg alcohol mixture per hour and liter of catalyst in a reactor according to Example 1 with the use of dehydration catalyst II. The results of the dehydration and the composition of the individual fractions are stated in Table V.

EXAMPLE 5

The dehydration of an ethanol-propanol fraction obtained according to the procedure of Example 3 was carried out according to the procedure of Example 4. The results of the dehydration and the composition of the individual fractions are listed in Table V.

TABLE I

Composition of promoted copper-, zinc-, aluminum- and potassium- containing catalysts (wt. %).

| Designation | CuO | ZnO | $Al_2O_3$ | K | $Cr_2O_3$ | MnO | GV* | BET Surface $(m^2/g)$ |
|---|---|---|---|---|---|---|---|---|
| A | 32.0 | 31.6 | 12.8 | 2.9 | 4.2 | 8.6 | 5.7 | 60.9 |
| B | 32.0 | 27.3 | 12.8 | 2.8 | 8.6 | — | 5.7 | 18.3 |
| C | 38.1 | 29.3 | 14.5 | 2.7 | 8.2 | — | 6.7 | 43.2 |
| D | 39.4 | 30.3 | 15.1 | 2.8 | 3.0 | — | 7.3 | 45.4 |

*GV = Loss on ignition, due mainly to carbon.

TABLE II

CO conversion (mol. %) and selectivities (%) of the formation of individual reaction products at 350° C., 100 bar pressure and at the space velocity of 2000 liters synthesis gas per hour and liter of catalyst.

| Catalyst | CO conversion (mol. %) | Selectivity (%) of the formation of | | | |
|---|---|---|---|---|---|
| | | Methanol | Higher aliph. alcohols | $CO_2$ | By-products ($CH_4$ + liquid hydrocarbons) |
| A | 41.3 | 42.2 | 11.8 | 44.5 | 1.5 |
| C | 42.1 | 39.5 | 18.5 | 37.8 | 4.2 |
| D | 33.8 | 45.8 | 16.2 | 36.1 | 1.9 |

TABLE III

Yield (g per hr and liter cat. and $m^3$ synthesis gas) of liquid reaction products, methanol and higher aliphatic alcohols

| Catalyst | Liquid reaction products | Methanol | Higher aliphatic alcohols of which | | | Percentage of ethanol in $C_2 + C_3$ alcohol fraction |
|---|---|---|---|---|---|---|
| | | | Total | $C_2 + C_3$ | $C_4 - C_6$ | |
| A | 67.3 | 48.1 | 13.1 | 10.3 | 2.8 | 48.5 |
| C | 73.7 | 47.9 | 21.9 | 11.6 | 10.3 | 36.1 |
| D | 64.4 | 39.7 | 19.4 | 11.2 | 8.2 | 25.6 |

TABLE IV

Composition of the ethanol-propanol fraction obtained

| | Synthesis catalyst | | |
|---|---|---|---|
| | A | C | D |
| | Composition of the ethanol-propanol fraction | | |
| Alcohol | 1 | 3 | 4 |
| Ethanol | 46.6 | 34.4 | 24.1 |
| n-Propanol | 4.7 | 3.5 | 3.5 |
| i-Propanol | 44.7 | 57.1 | 66.3 |
| $C_4$-$C_6$ alcohols | 4.0 | 5.0 | 6.1 |

TABLE V

Results of the dehydration of ethanol-propanol fraction

| Dehydration catalyst | Ethanol-propanol fraction | Conversion (mol. %) | B-products (wt. %) | Composition of the gaseous products (vol. %) | | |
|---|---|---|---|---|---|---|
| | | | | $C_2H_4$ | $C_3H_6$ | Higher olefins |
| I | 1 | 90.5 | 3.0 | 53.9 | 43.7 | 2.4 |
| I | 4 | 91.0 | 4.8 | 30.5 | 68.1 | 1.4 |
| II | 1 | 89.0 | 2.0 | 54.5 | 44.2 | 2.3 |
| II | 4 | 89.8 | 2.5 | 30.7 | 68.0 | 1.3 |

Many modifications will occur to those skilled in the art from the detailed description hereinabove given. This description is meant to be exemplary and non-limiting except insofar as being commensurate in scope with the appended claims.

We claim:

1. A process for production of $C_2$ and $C_3$ olefins from synthesis gas, which comprises:
   A. forming a mixture of methanol and higher alcohols especially rich in $C_2$ and $C_3$ alcohols in a first synthesis stage, which comprises the steps of:
      1. passing a synthesis gas mixture of carbon oxides and hydrogen at a temperature in the range of about 250° C. to 400° C. and at a pressure in the range of from about 80–150 bar, over a catalyst comprising:
         a. a major portion by weight of the oxides of copper and zinc, and a minor portion by weight of aluminum oxide, all in intimate association with each other,
  b. a promotional amount of a promoting compound selected from the group consisting of chromium, cerium, lanthanum, and manganese, and
  c. a compound of potassium in a weight concentration of from 0.03–3.4% (calculated as $K_2O$) based on the weight of the total catalyst;
B. separating the mixture of alcohols from the gas phase materials:
C. separating the methanol and higher alcohols into a methanol fraction and a higher alcohol fraction rich in $C_2$ and $C_3$ alcohols;
D. converting the higher alcohol fraction into olefins rich in $C_2$ and $C_3$ olefins in a dehydration stage, which comprises the steps of:
  1. passing said higher alcohol fraction over an alkalized dehydration catalyst at a low pressure and at a temperature in the range of from 350° C. to 500° C. and at a space velocity in the range of from 1–7 volumes of gas per volume of catalyst per hour, and
  2. separating the olefins from the non-olefinic materials.

2. A process as defined in claim 1, in which the oxides of copper and zinc are derived through
  A. coprecipitation of insoluble salts from an aqueous solution of soluble salts and
  B. calcination of said insoluble salts to convert said salts to their oxides.

3. A process, as defined in claim 1, in which the oxides of copper and zinc are derived by the decomposition of an amine complex containing copper and zinc to heat decomposable salts of copper and zinc followed by conversion of said salts to their oxides.

4. A process, as defined in claim 1, in which:
  A. the copper oxide is present in a concentration of about 18–45 weight %;
  B. zinc oxide is present in a concentration of about 24–50%;
  and
  C. aluminum oxide is present in a concentration of about 5–25 weight %.

5. A process, as defined in claim 1, in which said catalyst includes copper and zinc in an atomic ratio of between about 0.4–1.9:1.

6. A process, according to claim 1, in which the promoter compounds are present in quantities of about 1–25 weight %, calculated as the oxide.

7. A process, as defined in claim 2, in which the insoluble salts of copper and zinc are calcined at a temperature in the range of from 350°–400° C. to convert same to their oxides and said oxides are thereafter formed into shaped catalysts.

8. A process, as defined in claim 1, in which said catalysts are dipped into a solution of a soluble promoting material and thereafter are again calcined at a temperature of from 350°–450° C.

9. A process, as defined in claim 8, in which the impregnated and calcined catalysts are reimpregnated with a soluble salt of potassium and the catalysts are thereafter calcined at a temperature in the range of from 350°–450° C.

10. A process, as defined in claim 1, in which the synthesis gas in said synthesis stage is passed over the catalyst at a space velocity of about 500–5000 volumes:-volume of catalyst per hour and in which the process gas contains about 20–30 volume % of carbon monoxide, 0–20% of inert gases and 80–50% of hydrogen.

11. A process, as defined in claim 1, in which the dehydration catalyst comprises an alkalized aluminum oxide.

12. A process, as defined in claim 1, in which the dehydration catalyst comprises an alkalized calcium phosphate.

13. A process, as defined in claim 1, in which said dehydration catalyst is made by impregnation of a metal compound with a hydroxide or carbonate of an alkali metal.

14. A process, as defined in claim 1, in which the concentration of potassium expressed as the oxide is in the range of from 0.1–1.5 weight %.

15. A process, as defined in claim 1, in which the pressure of the process in the dehydration stage is in the range of 0.5–1 bar.

16. A process, as defined in claim 1, in which the reaction mixture, from the second stage of said process, is first cooled to a temperature of about 10° C. and separated by a liquid-gas separation of the gaseous and liquid products.

17. A process, as defined in claim 16, in which the gaseous products from said liquid-gas separation, are fractionated by low-temperature distillation.

18. A process, as defined in claim 1, in which the liquid products from said gas-liquid separation, are further fractionated by distillation or by extractive distillation.

19. A process for the production of olefins, as defined in claim 1, in which the products of conversion from the synthesis gas stage, are subjected to a cold gas cooling in step B of said process.

20. In the process for the production of $C_2$ to $C_3$ olefins from synthesis gas, as defined in claim 1:
  A. the improvement of increasing the concentration of ethylene in the olefin mixture which comprises:
  B. passing said synthesis gas over the catalyst of claim 1 in which the promoting compounds comprise the oxides of chromium and manganese.

21. In the process for the production of $C_2$ and $C_3$ olefins from synthesis gas as defined in claim 1:
  A. the improvement of increasing the concentration of propene in the olefin mixture which comprises:
  B. passing the said synthesis gas mixture over the catalyst of claim 1, in which the promoting compounds include the oxides of chromium.

* * * * *

UNITED STATES PATENT AND TRADEMARK OFFICE
CERTIFICATE OF CORRECTION

PATENT NO. : 4,398,050

DATED : August 9, 1983

INVENTOR(S) : Carl-Ernst Hofstadt, Michael Schneider and Karel Kochloefl

It is certified that error appears in the above-identified patent and that said Letters Patent is hereby corrected as shown below:

On the title page,

IN THE ABSTRACT

Lines 11 + 17    Place a comma after "Thereafter"

Col. 2, lines 25,
34, 39 and 46    Correct the spelling of "promoter"

Signed and Sealed this

Eighteenth Day of October 1983

[SEAL]

Attest:

GERALD J. MOSSINGHOFF

Attesting Officer    Commissioner of Patents and Trademarks